United States Patent
Bonnet et al.

(10) Patent No.: US 7,423,537 B2
(45) Date of Patent: Sep. 9, 2008

(54) PROCEDURE AND SYSTEM FOR DETECTING A PERSON'S FALL

(75) Inventors: Stephane Bonnet, Seyssinet (FR); Regis Guillemaud, La Tronche (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/446,356

(22) Filed: Jun. 5, 2006

(65) Prior Publication Data
US 2006/0279426 A1 Dec. 14, 2006

(30) Foreign Application Priority Data
Jun. 7, 2005 (FR) .................................. 05 51521

(51) Int. Cl.
*G08B 23/00* (2006.01)

(52) U.S. Cl. ................. 340/573.1; 340/573.7; 340/689; 600/301

(58) Field of Classification Search .............. 340/573.1, 340/573.7, 689, 506, 539.1, 576, 686.1; 128/904, 128/903; 600/300, 301, 483, 503
See application file for complete search history.

(56) References Cited

U.S. PATENT DOCUMENTS

| | | | | |
|---|---|---|---|---|
| 4,779,461 A | * | 10/1988 | Gilman et al. ............. 73/865.3 |
| 4,894,923 A | * | 1/1990 | Cobern et al. ................. 33/304 |
| 5,515,858 A | * | 5/1996 | Myllymaki ................. 600/301 |
| 5,940,004 A | * | 8/1999 | Fulton .................... 340/825.49 |
| 6,433,690 B2 | * | 8/2002 | Petelenz et al. .......... 340/573.1 |
| 7,150,048 B2 | * | 12/2006 | Buckman ....................... 2/465 |
| 2002/0008630 A1 | | 1/2002 | Lehrman et al. | |
| 2002/0103610 A1 | | 8/2002 | Bachmann et al. | |
| 2005/0027216 A1 | | 2/2005 | Guillemaud et al. | |

FOREIGN PATENT DOCUMENTS

| | | |
|---|---|---|
| EP | 1 493 385 A1 | 1/2005 |
| FR | 2 829 862 | 3/2003 |

OTHER PUBLICATIONS

Bob Kemp, et al., "Body position can be monitored in 3D using miniature accelerometers and earth-magnetic field sensors", Electroencephalography and clinical Neurophysiology, XP-002367000, vol. 109, 1998, pp. 484-488.

\* cited by examiner

*Primary Examiner*—Anh V La
(74) *Attorney, Agent, or Firm*—Oblon, Spivak, McClelland, Maier & Neustadt, P.C.

(57) ABSTRACT

A person under supervision wears a sensor consisting of at least one accelerometer (31) and a magnetometer (41), oriented in his vertical direction. A fall event is picked up when a significant and rapid oscillation of the acceleration signal coincides with a shift in the ambient magnetic field between two levels (between t=4000 and t=5000). Additional criteria that may also make use of the magnetometer enable the diagnosis to be made, and it is easier and safer to establish this than with accelerometers alone.

18 Claims, 4 Drawing Sheets

PROCEDURE AND SYSTEM FOR DETECTING A PERSON'S FALL

BACKGROUND OF THE INVENTION

1. Field of the Invention

The invention relates to a procedure and system for detecting when a person falls. It will be especially useful in medical institutions taking care of elderly people.

2. Discussion of the Background

There already exists a wide range of systems and procedures that monitor a person's activity and even detect a critical state requiring intervention. In general, one or more sensors are placed on the person and these continually transmit signals about his/her physical activity. Such signals typically take measurements of acceleration in one or more directions: hence a fall appears as a sharp change, generally involving a series of oscillations of short duration in at least one of the acceleration signals. An example of this is patent U.S. Pat. No.-B2-6,703,939.

One pitfall frequently encountered with systems of this kind is that it is difficult to determine what kinds of things have happened to the person wearing the sensor from the signals that it transmits. If a fall is characterized by an acceleration in the vertical direction, then actions involving bending or sitting give a similar response. When lying down the wearer naturally reproduces a movement that resembles a fall. Certain criteria distinguishing between an accidental fall and normal activities have been identified, but they are inadequate. Hence improvements are eagerly awaited by specialists. The invention represents such an improvement. In the procedure detecting a fall, measurement of the acceleration signal is supplemented by measuring signals of a different kind, whose combination gives a more reliable indication of the fall.

SUMMARY OF THE INVENTION

The invention involves using at least one magnetometer in the sensor worn by the person, in addition to the accelerometer. The magnetometer measures the ambient magnetic field and hence gives a reading which is completely different from that of the accelerometer recording the activity of the wearer.

The measurements yielded by the magnetometer are not sensitive to accelerations experienced by the sensor but only to changes in orientation. The measurements yielded by the magnetometer depend on the sensor's orientation in space: for example, when there is no magnetic disturbance, such as the presence of a ferromagnetic object in the person's vicinity, the projection of the Earth's magnetic field on each of the axes recorded by the sensor is measured. In particular, it has been noted that, during the instability period of the acceleration signal which characterizes a fall and some normal activities of the person, measurement of certain components of the magnetic-field signal showed a gradual transition between two different levels of magnetic field measurement, stable before and after the instability period when a fall actually occurred, and measurement of the acceleration signal and the difference in the magnetic-field measurement both before and after the instability together offered a good chance of pinpointing the fall by eliminating a significant number of events normally confused with it.

The invention can be applied in many ways. In particular, further criteria can be added to supplement the appraisal fall events and so give an even more reliable indication.

For signals measured and monitored continuously, these criteria may generally be useful if changes in the signals exceed a threshold for a particular period of time, for example in terms of signal strength or energy.

Signals that can be usefully measured are the vertical component of acceleration and the vertical component of the ambient magnetic field, measured in a frame associated with the person—from head to foot—and not measured with respect to the Earth. Falling from an upright pose is always accompanied by such a vertical acceleration, and measurement of the vertical component of the ambient magnetic field changes from a stable value in the standing position to a value that is usually different after a fall, the vertical component associated with the person then being part of the horizontal ground reading.

It is understood that, in order for the above and other criteria to be reliable, the instability period of the acceleration signal must be followed by a stable signal of sufficient duration, which may imply a loss of consciousness; if not, the event associated with the instability, whatever its nature, is not considered serious and is ignored by the procedure.

Other criteria for detecting a fall may include detecting a horizontal position when the acceleration signal is stable, for example by measuring the acceleration due to gravity as being effectively zero in the person's vertical direction.

The criteria may also include recognizing certain normal events that are likely to be confused with a fall. A common occurrence of this type is when the person goes to bed. In this instance and in others, the recognition criterion can include measuring a person's azimuth, that is, his/her orientation in the horizontal plane. In the circumstances in which the invention is usually used the wearer has only a small number of places in which to lie down, and these can easily be located previously. A fall will produce any azimuth whatsoever unlike normal reclining where the person's orientation is characterized by a known azimuth.

Discriminating normal events can be achieved not only by measuring the final state but also by examining an entire section of a signal, as events such as going to bed are generally accompanied by regular actions which impart an electronic character, that is, an electronic signature to the signals.

In general terms, a fall may be indicated by a numerical combination weighted by the criteria deployed. If the numerical threshold is exceeded by this combination, a fall will be signalled and the alert given.

BRIEF DESCRIPTION OF THE DRAWINGS

The invention involves another system capable of implementing the procedure.

DETAILED DESCRIPTION OF THE PREFERRED EMBODIMENTS

Figure 1:
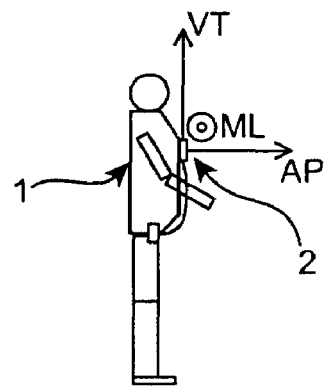
FIG. 1 illustrates use of the sensor.
Figure 2:
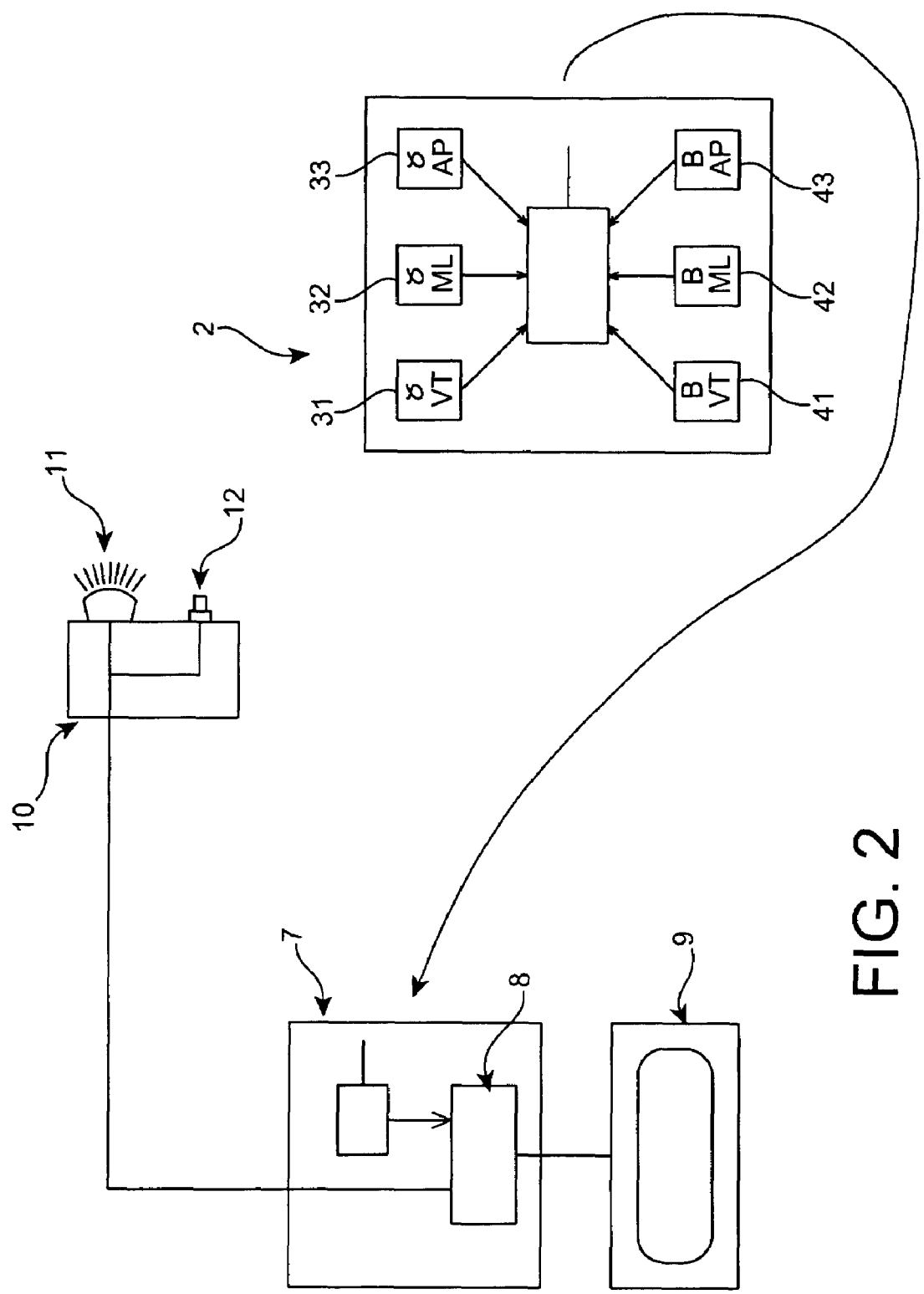
FIG. 2 is an overview of the system.

FIG. 1 represents a person 1 to be supervised according to the procedure and marked with a frame consisting of a vertical axis VT extended from head to foot, an antero-posterior axis AP projecting forward and medio-lateral axis ML projecting sideways. The origin of the axes is presumed to be on the body of person 1, for example on the chest or hip where there is a sensor 2, the arrangement of which is given in greater detail in FIG. 2. It contains three accelerometers 31, 32 and 33 which measure the accelerations they undergo, including gravity, along the three orthogonal axes of the frame, and three magnetometers 41, 42 and 43 which measure the components of the ambient magnetic field, essentially the Earth's natural magnetic field, along the three orthogonal axes of the frame. It is important to orient sensor 2 correctly on person 1, so that the measurement axes of accelerometers 31, 32 and 33 and of magnetometers 41, 42 and 43 coincide with the directions in the frame of person 1. Alternatively, sensor 2 can be placed in any orientation but should be measured using a calibration method (by placing the person 1 in a fixed position with respect to the ground and by using the measurements of the sensor 2 in this position), and the readings of the sensors would then be adjusted to align with the three axes of the frame. The readings, adjusted or not, of accelerometers 31, 32 and 33 and of magnetometers 41, 42 and 43 are transmitted by a transceiver to an examination station 7 which contains a special fall-detection processor 8 whose operation will be described below. Initially, when a fall is detected, it is transmitted to a local display device 9 to raise the alarm and to an alarm device 10 which may include lights 11, sirens etc. and a button 12. The alarm device 10 is located in a place visible by person 1 who has the option of cancelling a false alarm by pressing button 12. In its basic form, the alarm is linked to a remote medical assistance unit which can activate the rescue of person 1. In a more advanced and useful version, processing is engaged: the alarm-control device is situated on the patient's body.

A strong variation in amplitude, either of duration or frequency, measured by the accelerometers and especially the vertical accelerometer, is associated with a movement inflicting an impact on the sensor (fall, step, jump, etc.). A change in the value of the magnetic-field projection along the sensor's axes is associated with a change in the person's orientation, such as in a fall, going to bed, or the action of bending down.

The occurrence of the two events in a short space of time, of the order of a few seconds, for example 2 seconds, is a strong indication of a fall.

Figure 3A:
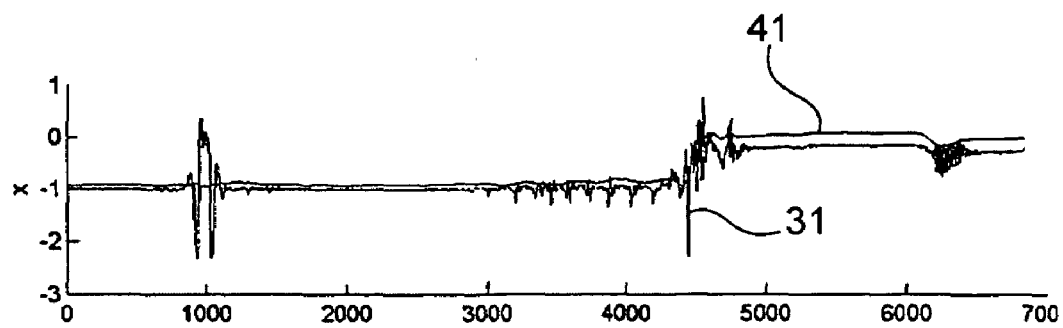
FIG. 3, consisting of diagrams 3A, 3B and 3C, illustrates a basic instance of detection, FIG. 4, consisting of diagrams 4A, 4B and 4C, illustrates a special instance of detection in the procedure.
Figure 3B:
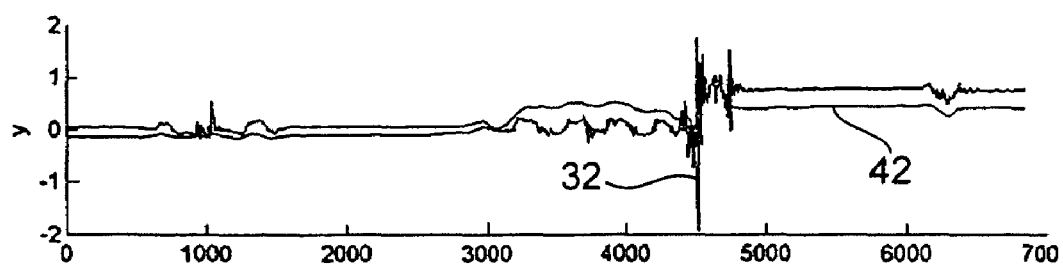
Figure 3C:
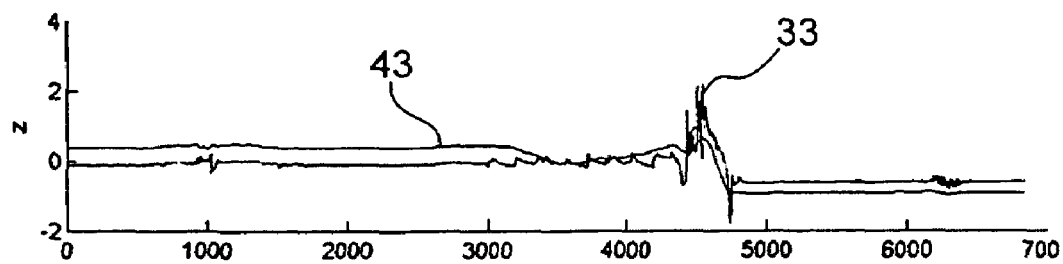

The sensor measurements may be those given in FIG. 3 in which the first diagram 3A shows the readings of accelerometer 31 and of magnetometer 41 in the vertical axis VT, diagram 3B shows the readings of accelerometer 32 and of magnetometer 42 in the medio-lateral axis ML, and diagram 3C shows the readings of accelerometer 33 and of magnetometer 43 in the antero-posterior axis AP. The sensor's range of measurements is about ±5 g for the accelerometers and about 50 micro-Teslas for the magnetometers. There are detectors on the market which can be used without any particular difficulty. An example is the tri-axial LIS3L02AQ accelerometer from ST Micro Electronics. In this example the accelerometer readings yield mainly periods of stability punctuated by shorter periods of instability in which an acceleration causes short but significant oscillations. These periods of instability number two here and correspond to two different events: the first, recorded at about time t=1000, is a leap taken by person 1; the other, recorded between about t=4000 and 5000 is a fall. These two events are rather indistinct in terms of acceleration readings, especially in the vertical axis VT which is precisely the one which most easily identifies a fall; but it is noted that the readings from magnetometers 41, 42 and 43 almost ignore the jump, whereas they show a significant change in the case of the fall which is particularly visible in the vertical component of diagram 3A. More precisely, the reading from magnetometer 41 in the vertical axis VT shows two plateaux at different levels before and after the fall, and this is linked to a gradual and fairly regular change in the instability readings of the acceleration signal. Diagrams 3B and 3C reveal that a similar conclusion about the occurrence of a fall can generally be reached in the same way by using magnetometers 42 and 43 placed along axes other than the vertical VT; however, there appears to be an exception when the fall does not involve a change in the angle made by the vertical axis with the direction of the ambient magnetic field, and this may mean measuring the magnetic field with at least two magnetometers oriented in different directions for greater reliability; it may be noted here that the change in the strength of the measurement made by magnetometer 42 in the medio-lateral axis ML is not very significant, and this may mean that the fall goes unnoticed if only the measurements associated with this axis are taken into account.

Efforts are being made to obtain a good discrimination between an accidental fall and other events resembling it in the signals transmitted. An additional criterion which it is interesting to deploy in this respect is to verify that person 1 is lying flat after the fall—and this is usually the case with only a few exceptions.

A horizontal position can be verified if accelerometer 31 in the vertical axis VT gives an effectively zero reading after the event assumed to be a fall, which means that it is perpendicular to the direction of gravity. This verification is made here after about time t=5000.

An effort can be made to differentiate the downward motion of person 1 who lies down, particularly when going to bed. Magnetometric measurements are useful here too, as the azimuth of person 1 or his horizontal orientation with respect to the ground will be uniform to within a few degrees when he is normally in bed. A reading of the results from magnetometers 41 and 42 arranged along the vertical axis VT and the medio-lateral axis MT is taken at the same time, approx. t=5000, to deduce the azimuth of person 1. If it differs from that of a person lying normally, a fall may be presumed.

If the reading from the final azimuth is lacking, a criterion that is almost as interesting may be obtained by comparing the changes in azimuth between the initial and final positions.

Figure 4A:
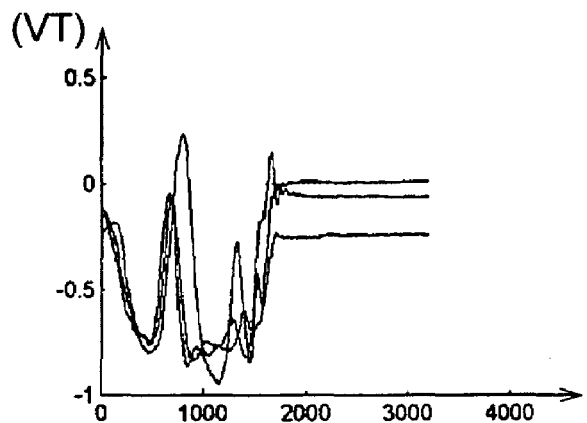
Figure 4B:
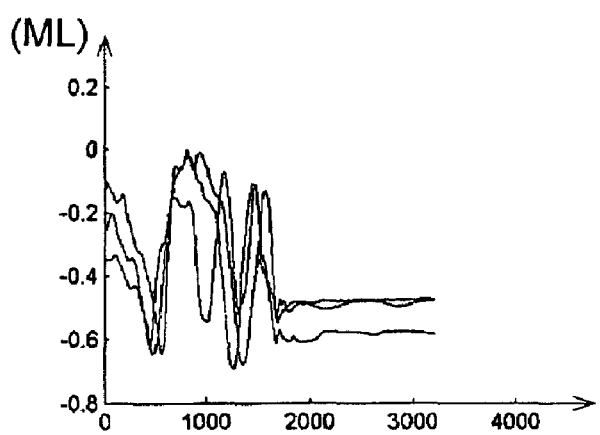
Figure 4C:
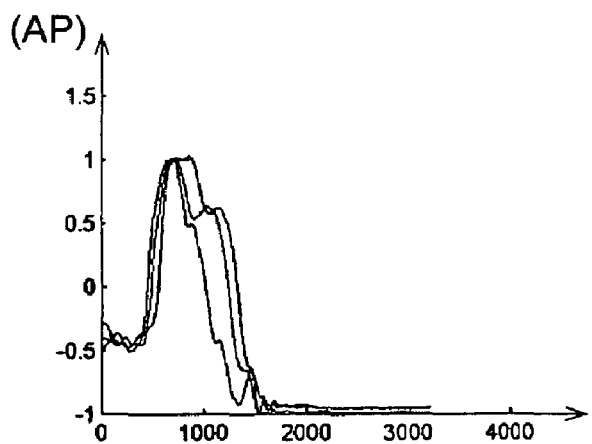

It is also possible to use sensor 2 to recognize the normal occurrence of going to bed. Diagrams 4A, 4B and 4C of FIG. 4 illustrate, respectively, the results from magnetometers 41, 42 and 43 along the vertical axes VT, the medio-lateral axis ML and the antero-posterior axis AP for a series of instances when person 1 went to bed. It is noted that the signals recorded at different times for the same action are very similar and may yield an electronic signal for the action, as person 1 always executes more or less the same motions. It is possible to detect a stage when he sits down between time t=0 and approx. t=700 (in diagram 4A), whilst turning (in diagram 4B) and leaning forward (at approx. t=500 in diagram C), before turning again until t=1700 (in diagrams 4A and 4C). The signature recorded by preliminary calibrations may involve both parts of the event, as distinguished above, or only the second which is more characteristic. These signals can then be compared with the interesting parts of equivalent signals obtained similarly with the same detectors and in the same environment, by using classical techniques for correlating signals.

Figure 5:
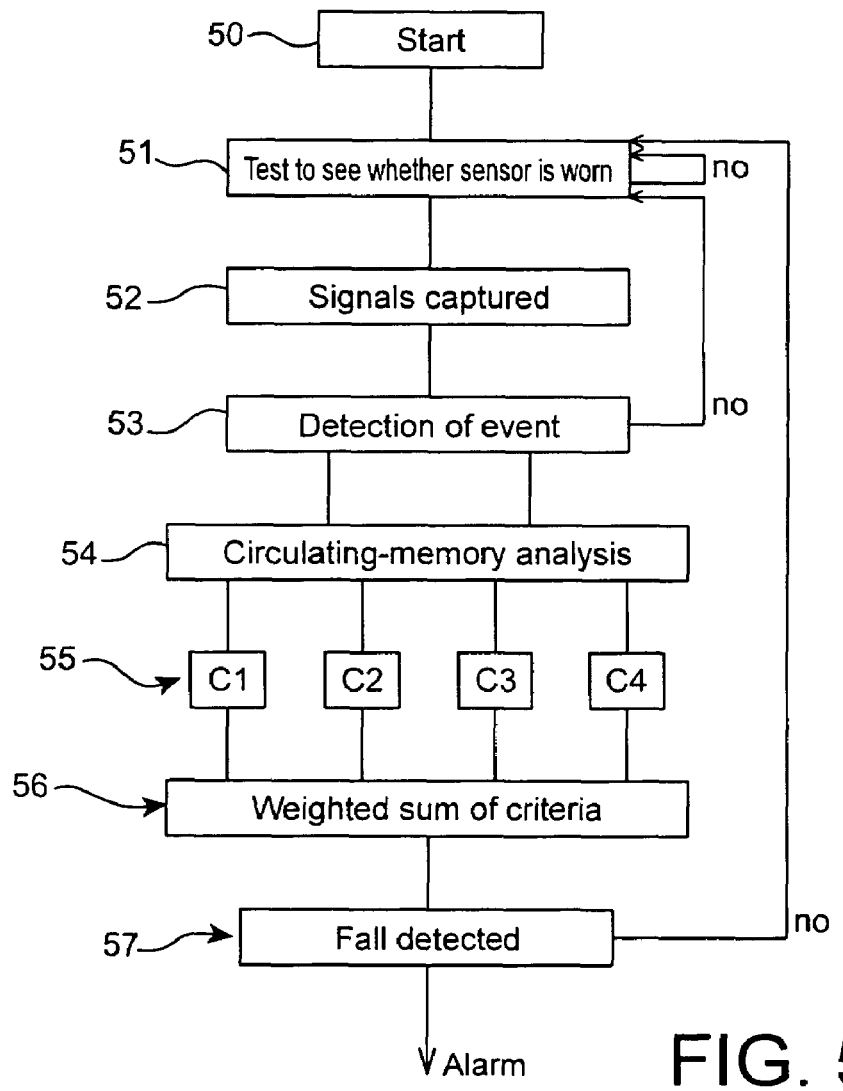
FIG. 5 is a diagram summarizing the procedure.

FIG. 5 illustrates how the procedure works. After initialisation at stage 50, a test 51 is carried out periodically to check whether sensor 2 is worn regularly. If so, the readings from sensor 2 pass to stage 52. The results are stored in the circulating memory of a processor 8 for about five minutes. If no event is recorded in the following stage 53, the system returns to stage 51 and runs in a loop. But when an event is recorded at stage 53, such as a sharp change in the accelerometer's signal, a significant change in the signals from the magnetometers or the detection of a horizontal posture, an analysis 54 is made by the circulating memory according to the criteria previously indicated or some of them. In the present case these criteria may be reduced to four digital criteria C1, C2, C3 and C4 calculated at stage 55 and taking the value 0 or 1 according to whether they are deemed absent or present; intermediate values, corresponding to a fuzzy-logic analysis, may be suggested in doubtful cases.

The number of criteria used depends on the reliability of the desired result and on processing quality and power. The more criteria there are, the greater the reliability.

Criterion C1 detects whether the person is lying down by examining the vertical-acceleration signal. It is set at 1 if it is verified for a defined period of time. If a horizontal posture has already been verified, this criterion must be validated irrespective of how long the situation has obtained.

Criterion 2 corresponds to a period of vigorous activity undertaken by person 1 changing to a state of weak activity, and this is translated into oscillations or significant variations in the signals. If the weak activity is maintained for a specific period, this criterion is set at 1. The acceleration signal in the vertical axis VT is used. Other signals can be used.

Criterion 3 corresponds to a comparison of the person's azimuth after the event with the azimuth of the normal reclining position. If these azimuths differ beyond a certain degree of tolerance, the criterion is set at 1. It can be seen that magnetometers 41 and 42 were used.

Lastly, criterion C4 corresponds to a comparison of the movement inherent in the event with the signatures already recorded in certain typical and normal movements, according to the explanations given in FIG. 4. If these movements differ beyond a certain threshold, the criterion is set at 1.

The following stage, 56, is a weighted sum of criteria C1 to C4, according to the formula:

$$S = w1C1 + w2C2 + w2C2 + w3C3 = w3C4 + w3C4,$$

where the sum of the weighting factors w1 to w4 is equal to 1. If the sum S is greater than a certain threshold—this can be 0.5 but may be selected according to the sensitivity required and the degree of supervision of person 1—the alarm is triggered after the fall-detection stage 57. The system returns to stage 51 and continues to take readings whatever the diagnosis.

The invention claimed is:

1. A process for detecting a fall of a person, comprising the following steps:
   placing a sensor on the person, said sensor comprising at least one accelerometer and at least one magnetometer;
   monitoring an acceleration signal and an ambient magnetic field signal provided by the sensor;
   analyzing changes in said acceleration signal and said ambient magnetic field signal;
   indicating a fall when a plurality of criteria have been met, the criteria including:
   a) identifying the presence of a first period of instability in a vertical component of the acceleration signal, followed by a second period of instability in said vertical component of the acceleration signal; said vertical component being considered in a height direction of the person, and
   b) discriminating between a fall and other events by analyzing a portion of the ambient magnetic field signal during said first period and said second period.

2. The process according to claim 1, wherein the portion of the ambient magnetic field signal includes a component of the ambient magnetic field along said height direction.

3. The process according to claim 2, wherein said discriminating includes indicating that a fall did not happen when said component of the ambient magnetic field along said height direction does not vary above a threshold in said portion of the ambient magnetic field signal.

4. The process according to claim 1, wherein the criteria further include:
   c) detecting a recumbent position of the person if the vertical component of the acceleration signal is near zero during the second period.

5. The process according to claim 1, wherein said discriminating is performed by comparing said portion of the ambient magnetic field signal with equivalent portions of signals recorded previously and respectively corresponding to normal events.

6. The process according to claim 5, wherein said comparing is performed for a part of the portion of the ambient magnetic field signal, said part corresponding to either the first period of instability or the second period of stability.

7. The process according to claim 6, wherein said analyzing of the ambient magnetic field signal includes determining an azimuth of the person.

8. The process according to claim 7, wherein one of the normal events includes laying on a bed and said comparing includes comparing the azimuth of the person during the second period and an azimuth of the bed.

9. The process according to claim 1, wherein said indicating comprises indicating a fall after a threshold is crossed by a weighted numerical combination of the criteria.

10. The process according to claim 1, further comprising converting raw measurements of the sensor to express components of signal axes associated with the person and consisting of a vertical axis, an antero-posterior axis and a medio-lateral axis.

11. The process according to claim 1, wherein said sensor includes at least three accelerometers that measure acceleration in three orthogonal axes and at least three magnetometers that measure the ambient magnetic field in the three orthogonal axes.

12. The process according to claim 11, wherein said sensor has a range of measurement of about +/−5 g for the accelerometers and about 50 micro-Telsa for the magnetometers.

13. The process according to claim 1, wherein said monitoring is performed continuously.

14. The process according to claim 1, wherein said discriminating is performed by comparing said ambient magnetic field signal before and after at least one of said first and second periods of instability.

15. The process according to claim 14, wherein said discriminating is performed by identifying said fall when said ambient magnetic field signal shows two plateaus at different levels before and after said at least one of said first and second periods of instability.

16. The process according to claim 14, wherein said discriminating is performed by identifying said fall when said vertical component of said acceleration signal is effectively zero after said at least one of said first and second periods of instability.

17. The process according to claim 1, wherein said first and second periods of instability are defined by oscillations in said acceleration signal and are separated by a period of stability during which said acceleration signal is relatively constant.

18. The process according to claim 1, wherein said step of indicating comprises transmitting a signal to a display device, wherein said signal signals that said fall occurred, and said display device produces an alarm indicating that said fall occurred.

* * * * *